(12) United States Patent
Xia et al.

(10) Patent No.: US 7,632,869 B2
(45) Date of Patent: Dec. 15, 2009

(54) ANTIMICROBIAL COMPOSITIONS AND USES THEREOF

(75) Inventors: Erning Xia, Penfield, NY (US); Alyce K. Dobie, Williamson, NY (US); John Denick, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 1172 days.

(21) Appl. No.: 10/852,460

(22) Filed: May 24, 2004

(65) Prior Publication Data

US 2005/0260099 A1    Nov. 24, 2005

(51) Int. Cl.
*A01N 33/08*    (2006.01)
*A61K 31/13*    (2006.01)

(52) U.S. Cl. .................... 514/670; 514/667

(58) Field of Classification Search ................ 514/670, 514/667
See application file for complete search history.

(56) References Cited

U.S. PATENT DOCUMENTS

| | | | |
|---|---|---|---|
| 3,291,683 A | 12/1966 | Lamb | |
| 4,748,158 A | 5/1988 | Biermann et al. | 514/25 |
| 5,422,073 A | 6/1995 | Mowrey-McKee et al. | 422/28 |
| 5,500,186 A | 3/1996 | Mowrey-McKee et al. | 422/28 |
| 5,593,637 A | 1/1997 | Mowrey-McKee et al. | 422/28 |
| 5,756,045 A | 5/1998 | Mowrey-McKee et al. | 422/28 |
| 5,817,277 A | 10/1998 | Mowrey-McKee et al. | 422/28 |
| 6,162,393 A * | 12/2000 | De Bruiju et al. | 422/28 |
| 6,210,639 B1 | 4/2001 | Vlass et al. | 422/29 |
| 6,260,561 B1 | 7/2001 | Gartner et al. | |
| 6,448,062 B1 | 9/2002 | Huth et al. | 435/264 |

FOREIGN PATENT DOCUMENTS

| | | |
|---|---|---|
| EP | 0 533 552 | 3/1993 |
| WO | WO 88/02985 | 5/1988 |
| WO | WO 94/25426 | 11/1994 |
| WO | WO 2005/014491 | 2/2005 |

\* cited by examiner

*Primary Examiner*—Frederick Krass
*Assistant Examiner*—Sean Basquill
(74) *Attorney, Agent, or Firm*—Joseph Barrera

(57) ABSTRACT

The use of compositions containing one or more ether amine antimicrobial agents and/or ether amine derivative antimicrobial agents in an amount effective to disinfect and/or preserve medical devices is described. Solutions containing one or more ether amine antimicrobial agent- and/or ether amine derivative antimicrobial agent-containing compositions and methods of making and using the same are also described.

9 Claims, 2 Drawing Sheets

ANTIMICROBIAL COMPOSITIONS AND USES THEREOF

FIELD OF THE INVENTION

The present invention is directed toward the use of one or more antimicrobial agents in a composition useful for disinfection and preservation. More particularly, the present invention is directed toward the use of one or more antimicrobial agents in a solution useful for no-rub cleaning of contact lenses and for preservation of ophthalmic solutions and devices.

BACKGROUND OF THE INVENTION

Contact lenses in wide use today fall into two general categories, hard and soft. The hard or rigid corneal type lenses are formed from materials prepared by the polymerization of acrylic esters, such as poly(methyl methacrylate) (PMMA). The gel, hydrogel or soft type lenses are made by polymerizing such monomers as 2-hydroxyethyl methacrylate (HEMA) or, in the case of extended wear lenses, by polymerizing silicon-containing monomers or macromonomers. Both the hard and soft types of contact lenses are exposed to a broad spectrum of microbes during normal wear and become soiled relatively quickly. Contact lenses whether hard or soft therefore require routine cleaning and disinfecting. Failure to routinely clean and disinfect contact lenses properly can lead to a variety of problems ranging from mere discomfort when being worn to serious ocular infections. Ocular infections caused by virulent microbes such as Pseudomonas aeruginosa can lead to loss of the infected eye(s) if left untreated or if allowed to reach an advanced stage before initiating treatment.

U.S. Pat. No. 4,758,595 discloses a contact lens disinfectant and preservative containing a biguanide or a water-soluble salt thereof in combination with a buffer, preferably a borate buffer, e.g., boric acid, sodium borate, potassium tetraborate, potassium metaborate or mixtures of the same.

U.S. Pat. No. 4,361,548 discloses a contact lens disinfectant and preservative containing dilute aqueous solutions of a polymer; namely, dimethyldiallylammonium chloride (DMDAAC) having molecular weights ranging from about 10,000 to 1,000,000. Amounts of DMDAAC homopolymer as low as 0.00001 percent by weight may be employed when an enhancer, such as thimerosal, sorbic acid or phenylmercuric salt is used therewith. Although lens binding and concomitant eye tissue irritation with DMDAAC were reduced, it was found in some users to be above desirable clinical levels.

Despite the availability of various commercially available contact lens disinfecting systems such as heat, hydrogen peroxide, biguanides, polymeric biguanides, quaternary ammonium polyesters, amidoamines and other chemical agents, there continues to be a need for improved disinfecting systems. Such improved disinfecting systems include systems that are simple to use, are effective against a broad spectrum of microbes, are non-toxic and do not cause ocular irritation as the result of binding to the contact lens material. There is a particular need in the field of contact lens disinfection and ophthalmic composition preservation for safe and effective chemical agents with antimicrobial activity.

SUMMARY OF THE INVENTION

The present invention relates to compositions useful for no-rub cleaning of contact lenses, for disinfecting medical devices such as contact lenses, for preserving solutions such as ophthalmic solutions, pharmaceuticals, artificial tears and comfort drops against microbial contamination, and for preserving medical devices such as contact lenses. Compositions of the present invention are suitable for use with all types of contact lenses, including rigid gas permeable contact lenses. Compositions of the present invention formulated into no-rub contact lens cleaning solutions eliminate the need for user rubbing of the contact lens during cleaning and provides enhanced, rapid disinfection of the contact lens. No-rub cleaning and rapid disinfection of contact lenses leads to higher user compliance and greater universal appeal than traditional contact lens disinfecting and cleaning solutions.

The subject antimicrobial agent-containing compositions are effective in the manufacture of solutions that are non-toxic, simple to use and do not cause ocular irritation.

Accordingly, it is an object of the present invention to provide compositions useful in the manufacture of ophthalmic disinfecting systems.

Another object of the present invention is to provide a method for using compositions in the disinfection of medical devices.

Another object of the present invention is to provide compositions useful in ophthalmic systems for disinfecting contact lenses.

Another object of the present invention is to provide compositions useful in preserving ophthalmic systems from microbial contamination.

Another object of the present invention is to provide compositions useful in ophthalmic systems for disinfecting contact lenses with reduced or eliminated eye irritation.

Another object of the present invention is to provide a method of making compositions useful in ophthalmic systems.

Still another object of the present invention is to provide a method of making compositions useful as disinfecting and preservative agents.

These and other objectives and advantages of the present invention, some of which are specifically described and others that are not, will become apparent from the detailed description and claims that follow.

DETAILED DESCRIPTION OF THE INVENTION

Figure 1:
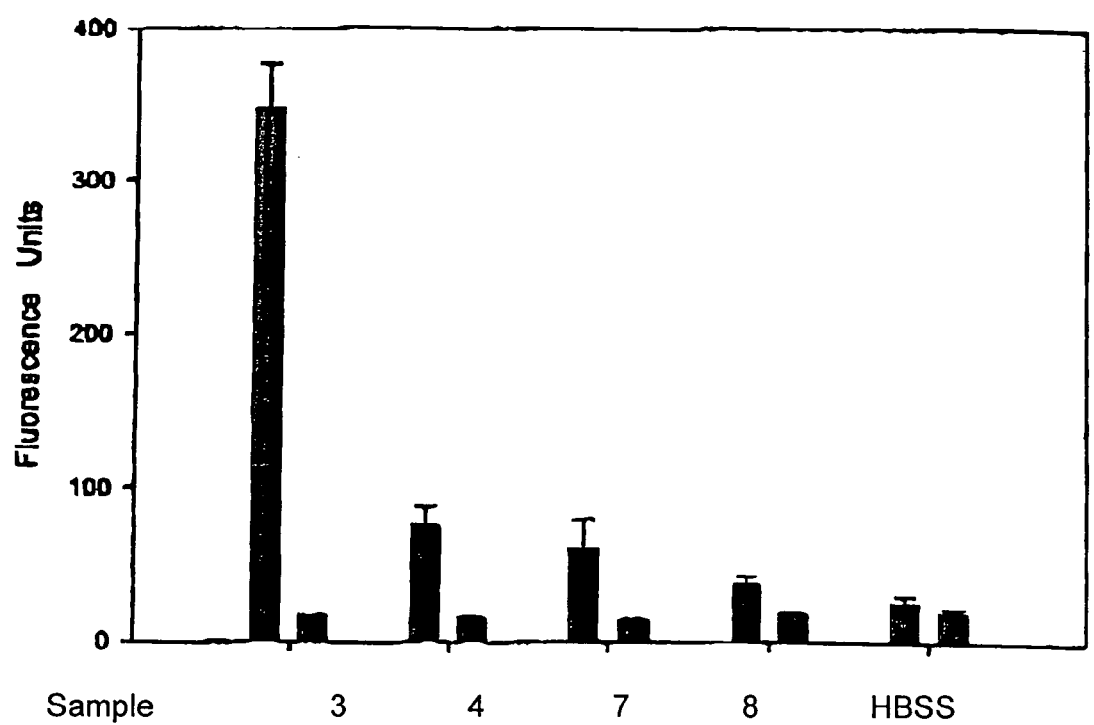
FIG. 1 is a graph depicting sodium-fluorescein assay and 24-hour recovery with fluorescence units vs. test solutions and control.

Compositions of the present invention can be used with all contact lenses such as conventional hard and soft lenses, as well as rigid and soft gas permeable lenses. Such suitable lenses include both hydrogel and non-hydrogel lenses, as well as silicone and fluorine-containing lenses. The term "soft contact lens" as used herein generally refers to those contact lenses that readily flex under small amounts of force. Typically, soft contact lenses are formulated from polymers having a certain proportion of repeat units derived from monomers such as 2-hydroxyethyl methacrylate and/or other hydrophilic monomers, typically crosslinked with a crosslinking agent. However, newer soft lenses, especially for extended wear, are being made from high-Dk silicone-containing materials.

Compositions of the present invention comprise one or more ether amine antimicrobial agents and/or ether amine derivative antimicrobial agents such as the dialkyl ether amine of the generalized structure illustrated in Formula 1 below.

FORMULA 1

Here, the R group is a $C_7$-$C_{24}$ alkyl group such as for example but not limited to heptyl, octyl or decyl; and the $R_1$ groups may be the same or different $C_1$-$C_2$ alkyl group for solubility. Compositions of the present invention contain from about 0.0001 to about 5.0 weight percent, but preferably from about 0.001 to about 1.0 weight percent and most preferably from about 0.025 to about 0.50 weight percent of one or more ether amine antimicrobial agents and/or ether amine derivative antimicrobial agents, such as for example dialkyl ether amine antimicrobial agents, based on the total weight of the composition. Suitable ether amine antimicrobial agents and/or ether amine derivative antimicrobial agents include for example but are not limited to N,N-dimethylaminopropyl decanoic ether and N,N-dimethylaminopropyl tridecanoic ether. N,N-dimethylaminopropyl decanoic ether and N,N-dimethylaminoproyl tridecanoic ether are available commercially from Tomah[3] Products, Inc., Milton, Wis. N,N-dimethylaminopropyl decanoic ether and N,N-dimethylaminopropyl tridecanoic ether are the preferred ether amine antimicrobial agents and/or ether amine derivative antimicrobial agents for use in compositions of the present invention due to their extensive moisture-binding properties and excellent substantivity, which serve to moisturize and soften ocular and/or nasal tissues, thus, increasing user comfort.

Compositions of the present invention are useful in a "no rub" regimen for cleaning and disinfecting contact lenses. Contact lens care compositions or solutions require disinfection compliance with the U.S. Food and Drug Administration (FDA) under the Premarket Notification (510 k) Guidance Document for Contact Lens Care Products, May 1, 1997 and International Standards Organization (ISO) 14729, International Standardized Document for Ophthalmic Optics. These guidelines utilize two steps, namely a stand-alone disinfection part and a regimen test procedure part. The stand-alone procedure measures the extent of viability loss of representative microorganisms at established time intervals to determine the extent of viability loss as is set forth in Example 3 below. The regimen test procedure is applicable to multi-functional disinfection solutions, which may include cleaning, rinsing and soaking, and is accomplished based on the regimen recommended by the manufacturer. The test organisms recommended by the FDA 510(k) Guidance Document and ISO 14729 include three bacteria, i.e., *Pseudomonas aeruginosa* ATCC 9027, *Stapylococcus aureus* ATCC 6538 and *Serratia marcescens* ATCC 13880, and two fungi, i.e., *Candida albicans* ATCC 10231 and *Fusarium solani* ATCC 36031.

The ether amine antimicrobial agent- and/or ether amine derivative antimicrobial agent-containing compositions of the present invention are useful for disinfecting medical devices. For example, the subject ether amine antimicrobial agent- and/or ether amine derivative antimicrobial agent-containing compositions are useful in contact lens care solutions for rapidly disinfecting contact lenses. For purposes of the present invention, "rapidly disinfecting" is defined as microorganism reduction of at least one log in about one hour. Compositions of the present invention are preferably in solution in sufficient concentration to destroy harmful microorganisms on the surface of a contact lens within a recommended minimum soaking time. This recommended minimum soaking time is included in the package instructions for use of the solution. The term "disinfecting solution" does not exclude the possibility that the solution may also be useful as a preserving solution, or that the disinfecting solution may be useful for other purposes such as daily no-rub cleaning, rinsing, and/or storage of contact lenses, depending on the particular formulation containing the subject compositions. Additionally, compositions of the present invention can be used in conjunction with other known disinfecting or preserving compounds if desired.

One or more compositions of the present invention in solution are physiologically compatible or "ophthalmically safe" for use with contact lenses. Ophthalmically safe as used herein means that a contact lens treated with or in the subject solution is generally suitable and safe for direct placement on the eye without rinsing. The subject solutions are safe and comfortable for daily contact with the eye via a contact lens that has been wetted with the solution. An ophthalmically safe solution has a tonicity and pH that is compatible with the eye and comprises materials, and amounts thereof, that are non-cytotoxic according to ISO standards and U.S. FDA regulations. The solution should be sterile in that the absence of microbial contaminants in the product prior to release should be statistically demonstrated to the degree necessary for such products.

In addition to one or more ether amine antimicrobial agents and/or ether amine derivative antimicrobial agents, compositions of the present invention may also include one or more buffers, or a buffering system to adjust the final pH of a solution containing said compositions. Suitable buffers include for example but are not limited to phosphate buffers, borate buffers, tris(hydroxymethyl)aminomethane (Tris) buffers, bis(2-hydroxyethyl)imino-tris(hydroxymethyl) methane (bis-Tris) buffers, sodium bicarbonate, and combinations thereof. A suitable buffering system for example may include at least one phosphate buffer and at least one borate buffer, which buffering system has a buffering capacity of 0.01 to 0.5 mM, preferably 0.03 to 0.45, of 0.01 N of HCl and 0.01 to 0.3, preferably 0.025 to 0.25, of 0.01 N of NaOH to change the pH one unit. Buffering capacity is measured by a solution of the buffers only. Such buffers are preferably present in a total amount of from approximately 0.02 to approximately 3.0 percent by weight based on the total weight of the composition. Other suitable buffers include for example but are not limited to monoethanolamine (MEA), diethanolamine (DEA), triethanolamine (TEA), 2-amino-2-methyl-1,3-propanediol (AMPD), 2-dimethylamino-2-methyl-1-propanediol (DMAMP), 2-amino-2-ethylpropanol (AEP), 2-amino-1-butanol (AB) and 2-amino-2-methyl-1-propanol (AMP). The pH of lens care solutions of the present invention is preferably maintained within the range of 5.0 to 8.0, more preferably about 6.0 to 8.0, most preferably about 6.5 to 7.8.

Compositions of the present invention may likewise include one or more tonicity agents to approximate the osmotic pressure of normal lachrymal fluids, which is equivalent to a 0.9 percent solution of sodium chloride or 2.5 percent glycerin solution. Examples of suitable tonicity agents include but are not limited to sodium and potassium chloride, dextrose, mannose, glycerin, calcium and magnesium chloride. These agents are typically used individually in amounts ranging from about 0.01 to about 2.5 percent w/v and, preferably, from about 0.2 to about 1.5 percent w/v. Preferably, the tonicity agent is employed in an amount to provide a final osmotic value of about 200 to about 450 mOsm/kg and more preferably between about 220 to about 350 mOsm/kg, and most preferably between about 220 to about 320 mOsm/kg.

Compositions of the present invention may likewise include one or more polyether agents. Polyether agents may be present in the subject compositions in a total amount of from approximately 0.001 to approximately 25.0 percent by weight based on the total weight of the composition, but more preferably from about 0.001 to about 5.0 percent by weight. Suitable polyether agents include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein in its entirety by reference. Suitable polyethers for use in the present composition should be soluble in solution, should not become turbid, and should be non-irritating to eye tissues.

The compositions of the present invention are described in still greater detail in the examples that follow.

EXAMPLE 1

Preparation of Sample Test Solutions

Sample solutions for testing were prepared in accordance with formulations of the present invention set forth below in Table 1.

TABLE 1

| | Sample Test Solutions | | | |
|---|---|---|---|---|
| Ingredients | Test Solution | | | |
| W/W Percent | 1 | 2 | 3 | 4 |
| Sodium Borate | 0.090 | 0.090 | 0.090 | 0.090 |
| Boric Acid | 0.850 | 0.850 | 0.850 | 0.850 |
| Sodium Chloride | 0.450 | 0.450 | 0.450 | 0.450 |
| Tetronic 1107 | 0.500 | 0.500 | 0.500 | 0.500 |
| Dimethyl Ether Amine (R = $C_{10}$) | 0.100 | 0.050 | 0.025 | 0.0125 |
| PH | 7.4 | 7.4 | 7.4 | 7.4 |
| Osmolality (mOsm/Kg) | 300 | 300 | 300 | 300 |
| Ingredients | Test Solution | | | |
| W/W Percent | 5 | 6 | 7 | 8 |
| Sodium Borate | 0.090 | 0.090 | 0.090 | 0.090 |
| Boric Acid | 0.850 | 0.850 | 0.850 | 0.850 |
| Sodium Chloride | 0.450 | 0.450 | 0.450 | 0.450 |
| Tetronic 1107 | 0.500 | 0.500 | 0.500 | 0.500 |
| Dimethyl Ether Amine (R = $C_{13}$) | 0.100 | 0.050 | 0.025 | 0.0125 |
| PH | 7.4 | 7.4 | 7.4 | 7.4 |
| Osmolality (mOsm/Kg) | 300 | 300 | 300 | 300 |

EXAMPLE 2

Biocidal Testing of Sample Test Solutions with Five FDA/ISO Challenge Microorganisms Test solutions prepared in accordance with Example 1 above, were each tested for ISO/FDA microbial biocidal efficacy using five FDA/ISO challenge microorganisms, i.e., three bacteria and two fungi. Primary acceptance criteria established for bacteria require that the number of viable bacteria, recovered per ml, shall be reduced by a value not less than 3.0 logs within the minimum recommended disinfection period. Primary acceptance criteria established for yeasts and molds require that the number of viable yeasts and molds, recovered per ml, shall be reduced by a value of not less than 1.0 logs within the minimum recommended disinfection time with no increase at not less than four times the minimum recommended disinfection time within an experimental error of +/−0.5 logs. Secondary acceptance criteria for bacteria requires that there is a combined log reduction for the mean values of all three bacteria of not less than 5.0 logs within the recommended disinfection period. The minimum acceptable mean log reduction for any single bacterial type is 1.0 log. Stasis for the yeast and mold must be observed for the minimum recommended disinfection period. Results of the ISO/FDA microbial biocidal efficacy testing of the subject test solutions are set forth below in Table 2. The results show that a 0.0125 concentration of the antimicrobial agent, i.e., Test Solutions 4 and 8, does not pass ISO/FDA microbial biocidal efficacy. Antimicrobial agent concentrations above 0.0125, i.e., Test Solutions 1-3 and 5-7, do pass ISO/FDA microbial biocidal efficacy.

TABLE 2

| Biocidal Efficacies | | | | | |
|---|---|---|---|---|---|
| | | Log Reduction of Test Solution | | | |
| ISO Agent | Hours | 1 | 2 | 3 | 4 |
| Staphylococcus aureus | 1 | >4.6 | 3.8 | 1.3 | ND |
| (ATCC 6538) | 4 | >4.6 | >4.6 | 3.1 | ND |
| Pseudomonas aeruginosa | 1 | >4.7 | >4.7 | >4.7 | 2.5 |
| (ATCC 9027) | 4 | >4.7 | >4.7 | >4.7 | >4.7 |
| Serratia marcescens | 1 | >4.6 | >4.6 | 2.5 | ND |
| (ATCC 13880) | 4 | >4.6 | >4.6 | 3.7 | 1.7 |
| Candida albicans | 1 | >4.7 | >4.7 | >4.7 | 2.3 |
| (ATCC 10231) | 4 | >4.7 | >4.7 | >4.7 | 3.6 |
| Fusarium solani | 1 | >4.3 | >4.3 | >4.3 | 2.1 |
| (ATCC 36031) | 4 | >4.3 | >4.3 | >4.3 | 2.8 |

ND = no data (failed)

| | | Log Reduction of Test Solution | | | |
|---|---|---|---|---|---|
| ISO Agent | Hours | 5 | 6 | 7 | 8 |
| Staphylococcus aureus | 1 | >4.6 | >4.6 | 4.6 | 2.5 |
| (ATCC 6538) | 4 | >4.6 | >4.6 | 4.6 | 4.7 |
| Pseudomonas aeruginosa | 1 | >4.7 | >4.7 | 4.3 | >4.7 |
| (ATCC 9027) | 4 | >4.7 | >4.7 | >4.7 | >4.7 |
| Serratia marcescens | 1 | 3.8 | 3.9 | 3.1 | 1.8 |
| (ATCC 13880) | 4 | 4.4 | 4.3 | 3.3 | 1.8 |
| Candida albicans | 1 | >4.7 | >4.7 | >4.7 | 4.2 |
| (ATCC 10231) | 4 | >4.7 | >4.7 | >4.7 | >4.7 |
| Fusarium solani | 1 | >4.3 | >4.3 | >4.3 | >4.3 |
| (ATCC 36031) | 4 | >4.3 | >4.3 | >4.3 | >4.3 |

EXAMPLE 3

ISO/FDA Stand-Alone Procedure for Disinfecting Products Using Five ISO/FDA Challenge Microorganisms The ISO/FDA Stand-Alone procedure for disinfecting products using 10 percent organic soil was conducted whereby test solutions were tested against *Pseudomas aeruginosa* ATCC 9027, *Staphylococcus aureus* ATCC 6538, *Serratia marcescens* ATCC13880, *Candida albicans* ATCC 10231 and *Fusarium solani* ATCC 36031. Primary acceptance criteria established for bacteria require that the number of viable bacteria, recovered per ml, shall be reduced by a value not less than 3.0 logs within the minimum recommended disinfection period. Primary acceptance criteria established for yeasts and molds require that the number of viable yeasts and molds, recovered per ml, shall be reduced by a value of not less than 1.0 logs within the minimum recommended disinfection time with no increase at not less than four times the minimum recommended disinfection time within an experimental error of +/−0.5 logs. Secondary acceptance criteria for bacteria requires that there is a combined log reduction for the mean values of all three bacteria of not less than 5.0 logs within the recommended disinfection period. The minimum acceptable mean log reduction for any single bacterial type is 1.0 log. Stasis for the yeast and mold must be observed for the minimum recommended disinfection period. The results of the Stand-Alone study are set forth below in Table 3. The results confirm that the presence of 10 percent organic soil does not decrease biocidal efficacies against all challenge organisms.

EXAMPLE 4

Toxicity Evaluation Using In-Vitro Sodium-Fluorescein Permeability Assay

Loss of tight corneal epithelium cell junctions and defects in the integrity of the corneal epithelium can be evaluated by using an in-vitro sodium-fluorescein permeability assay. To do so, five-tenths ml of a cell suspension containing $2 \times 10^5$ per ml cells were seeded in Millicel HA™ (Millipore Corporation, Billerica, Mass.) 13 mm inserts. The inserts were transferred into 24-well plates containing 0.5 ml of Dulbecco's Modified Eagles' Medium (DMEM) per well. The plates were then incubated at 37° C. with five percent carbon dioxide for six days. Fresh media was added to the wells and the inserts on days two through six. On day six, the inserts were used for the permeability assay. For the permeability assay, each insert was gently rinsed three times with 1 ml of Hank's Balanced Salt Solution (HBSS) without phenol red, using a 10 ml syringe without a needle. Five-tenths ml of the test solution was added to separate inserts, which had been placed in a fresh 24-well plate. Triplicate inserts were used for each test solution. The inserts were incubated in a 100 percent humidified chamber at 37° C. for thirty minutes. Each series of triplicate samples were handled sequentially to allow exact timing of treatment and subsequent steps. After incubation, each insert was individually rinsed five times with 1 ml HBSS using a 10 ml syringe without a needle. The inserts were then removed from the wells, and the amount of sodium-fluorescein was measured using a fluorometer at 540 nm excitation and 590 nm emission. Triplicate controls, i.e., HBSS-HBSS (HH), HBSS-test solution (HT) and MEM-MEM (MM), were run in the sequence and time as described above. The results of the assay are set forth below in Table 4 and are illustrated in FIG. 1. The results from the sodium-fluorescein permeability assay suggest that dimethyl ether amine-con-

TABLE 3

Efficacy of Test Solutions Using ISO/FDA Stand-Alone Procedure

| TEST ISO/FDA Stand-Alone (10% organic soil) | Test Solution | | | | | | | |
|---|---|---|---|---|---|---|---|---|
|  | 1 | 2 | 3 | 4 | 5 | 6 | 7 | 8 |
|  | Log Reduction | | | | | | | |
| *Pseudomas aeruginosa* | | | | | | | | |
| 1 Hour Soaking Time | >4.7 | >4.7 | >4.7 | 2.5 | >4.7 | >4.7 | 4.3 | >4.7 |
| 4 Hour Soaking Time | >4.7 | >4.7 | >4.7 | >4.7 | >4.7 | >4.7 | >4.7 | >4.7 |
| *Staphylococcus aureus* | | | | | | | | |
| 1 Hour Soaking Time | >4.6 | 3.8 | 1.3 | ND | >4.6 | >4.6 | 4.6 | 2.5 |
| 4 Hour Soaking Time | >4.6 | >4.6 | 3.1 | ND | >4.6 | >4.6 | 4.6 | 4.2 |
| *Serratia marcescens* | | | | | | | | |
| 1 Hour Soaking Time | >4.6 | >4.6 | 2.5 | ND | 3.8 | 3.9 | 3.1 | 1.8 |
| 4 Hour Soaking Time | >4.6 | >4.6 | 3.7 | 1.7 | 4.4 | 4.3 | 3.3 | 1.8 |
| *Candida albicans* | | | | | | | | |
| 1 Hour Soaking Time | >4.7 | >4.7 | >4.7 | 2.3 | >4.7 | >4.7 | >4.7 | 4.2 |
| 4 Hour Soaking Time | >4.7 | >4.7 | >4.7 | 3.6 | >4.7 | >4.7 | >4.7 | >4.7 |
| *Fusarium solani* | | | | | | | | |
| 1 Hour Soaking Time | >4.3 | >4.3 | >4.3 | 2.1 | >4.3 | >4.3 | >4.3 | >4.3 |
| 4 Hour Soaking Time | >4.3 | >4.3 | >4.3 | 2.8 | >4.3 | >4.3 | >4.3 | >4.3 |

Log Reduction: >= 100 percent kill
ND = no data (failed)

taining compositions do not interrupt or slightly interrupt tight corneal epithelium cell junctions and cell membranes of epithelium cells because the same is recovered after 24 hours.

TABLE 4

Sodium-Fluorescein Assay and Twenty-Four Hour Recovery

| Test Solution | Fluorescence Units | | | |
|---|---|---|---|---|
| 3 | 348.0000 | 29.0000 | 18.0000 | 0.0000 |
| 4 | 76.0000 | 12.0000 | 16.0000 | 1.0000 |
| 7 | 61.0000 | 19.0000 | 15.0000 | 1.0000 |
| 8 | 38.0000 | 5.0000 | 19.0000 | 1.0000 |
| HBSS | 25.0000 | 5.0000 | 19.0000 | 3.0000 |

EXAMPLE 5

Challenge of Sodium-Fluorescein Assay

Figure 2:
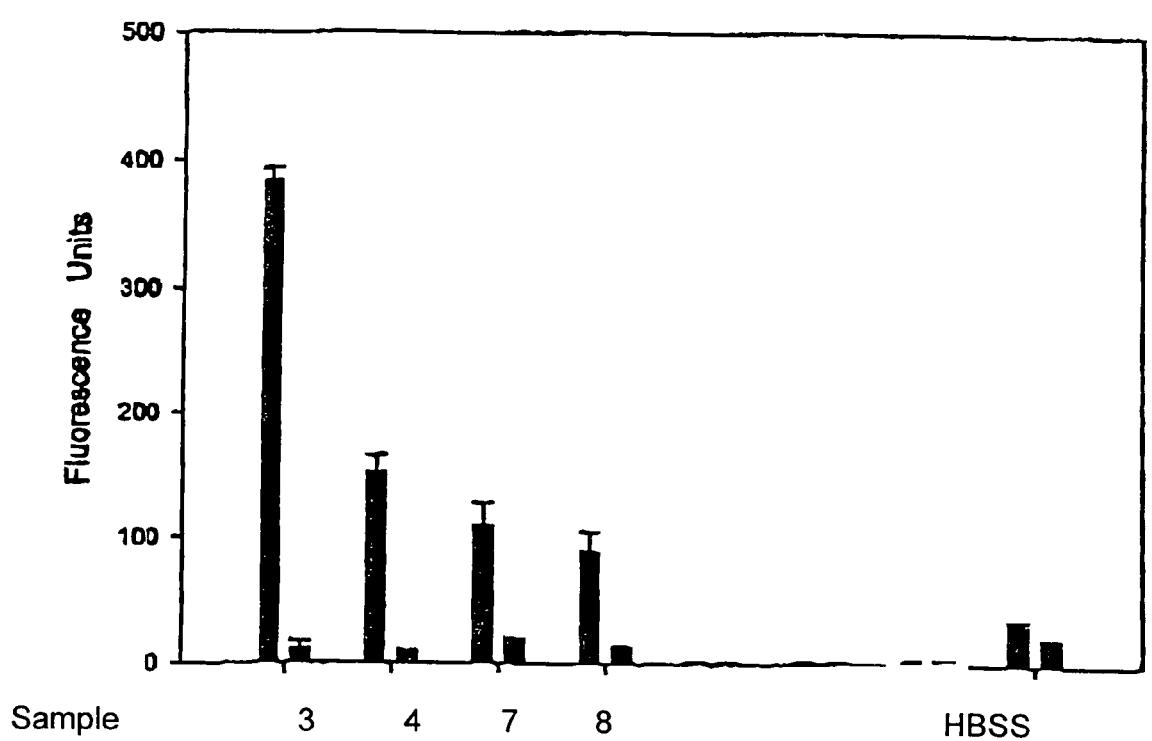
FIG. 2 is a graph depicting a challenge of the sodium-fluorescein assay with fluorescence units vs. test solutions and control.

The corneal epithelium cell junctions and the integrity of the corneal epithelium were evaluated by using the same in-vitro sodium-fluorescein permeability assay as described above in Example 4, with the exception that a 30 minute preincubation was used with test solutions, prior to challenge with sodium-fluorescein. The results of the assay are set forth below in Table 5 and are illustrated in FIG. 2. The results of the examples set forth herein suggest that dimethyl ether amine-containing compositions provide safe, fast and broad disinfection and/or preservation.

TABLE 5

Sodium-Fluorescein Assay Challenge

| Test Solution | Fluorescence Units | | | |
|---|---|---|---|---|
| 3 | 348.0000 | 10.0000 | 13.0000 | 5.0000 |
| 4 | 152.0000 | 14.0000 | 10.0000 | 1.0000 |
| 7 | 110.0000 | 18.0000 | 19.0000 | 1.0000 |
| 8 | 89.0000 | 16.0000 | 12.0000 | 2.0000 |
| HBSS | 33.0000 | 3.0000 | 17.0000 | 3.0000 |

Ether amine antimicrobial agent- and/or ether amine derivative antimicrobial agent-containing compositions of the present invention are useful as contact lens care solutions for no-rub cleaning and rapid disinfection of contact lenses. A disinfecting amount of one or more ether amine antimicrobial agents and/or ether amine derivative antimicrobial agents is an amount that will at least partially reduce the microorganism population in the formulations employed. Preferably, a disinfecting amount is that which will reduce the microbial burden of representative bacteria by two log orders in four hours and more preferably by one log order in one hour. Most preferably, a disinfecting amount is an amount that will eliminate the microbial burden on a contact lens when used according to its regimen for the recommended soaking time as established by ISO (International Standards for Ophthalmic Optics)/FDA Stand-Alone Procedures for Disinfection Test (ISO/DIS 14729; 2001). Typically, such agents are present in concentrations ranging from about 0.00001 to about 0.5 percent weight/volume (w/v), and more preferably, from about 0.00003 to about 0.5 percent w/v.

As stated above, contact lenses are cleaned without the need for manual rubbing and rapidly disinfected by contacting the lens with a solution of one or more compositions of the present invention. This is accomplished by simply soaking or immersing a contact lens in several milliliters of the subject solution. Preferably, the lens is permitted to soak in the solution for a period of at least one to four hours. The lenses are then removed from the solution, rinsed with the same or a different solution, for example a preserved isotonic saline solution and then replaced on the eye.

Solutions containing one or more compositions of the present invention may be formulated into specific contact lens care products for use as customary in the field of ophthalmology. Such products include but are not limited to wetting solutions, soaking solutions, cleaning and conditioning solutions, as well as multipurpose type lens care solutions and in-eye cleaning and conditioning solutions.

Solutions containing one or more compositions of the present invention may be formulated into specific products for disinfecting medical devices such as for example but not limited to contact lenses.

Products containing one or more compositions of the present invention may be formulated for preservation against microbial contamination such as for example but not limited to ophthalmic solutions, pharmaceuticals, artificial tears and comfort drops.

Solutions containing one or more compositions of the present invention may be formulated into specific products for preserving medical devices from microbial contamination such as for example but not limited to products formulated for the storage of contact lenses.

While the invention has been described in conjunction with specific examples thereof, this is illustrative only. Accordingly, many alternatives, modifications, and variations will be apparent to those skilled in the art in the light of the foregoing description and it is, therefore, intended to embrace all such alternatives, modifications, and variations as to fall within the spirit and scope of the appended claims.

We claim:

1. An ophthalmic composition comprising:
   0.001 wt. % to 1.0 wt. % of one or more ether amine antimicrobial agents of the generalized structure:

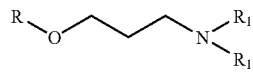

wherein the R group is a $C_7$-$C_{24}$ alkyl group; and the $R_1$ groups may be the same or different $C_1$-$C_2$ alkyl group, and one or more tonicity agents are present in an amount to provide a final osmotic value of about 200 to about 450 mOsm/kg.

2. The composition of claim 1 wherein at least one of said one or more antimicrobial agents is N,N-dimethylaminopropyl decanoic ether or N,N-dimethylaminoproyl tridecanoic ether.

3. The composition of claim 1 wherein said said wt % is about 0.025 to about 0.50 weight percent.

4. The composition of claim 1 further comprising one or more polyethers comprising PEO-PPO-PEO or PPO-PEO-PPO.

5. The composition of claim 1 further comprising one or more buffers wherein said one or more buffers are selected from the group consisting of phosphate buffers, borate buffers, citrate buffers, tris(hydroxymethyl)aminomethane buffers, bis(2-hydroxyethyl)imino-tris(hydroxymethyl)methane buffers, sodium bicarbonate, monoethanolamine, diethanolamine, triethanolamine, 2-amino-2-methyl-1,3-propanediol, 2-dimethylamino-2-methyl-1-propanediol, 2-amino-2-ethylpropanol, 2-amino-1-butanol and 2-amino-2-methyl-1-propanol.

6. The composition of claim 1 wherein said one or more tonicity agents are selected from the group consisting of sodium chloride, potassium chloride, dextrose, mannose, glycerin, calcium chloride and magnesium chloride.

7. The composition of claim 5 wherein said one or more buffers are selected from the group consisting of citrate buffers, tris(hydroxymethyl)aminomethane buffers, bis(2-hydroxyethyl)imino-tris(hydroxymethyl)methane buffers, 2-amino-2-methyl-1,3-propanediol, 2-dimethylamino-2-methyl-1-propanediol, 2-amino-2-ethylpropanol, 2-amino-1-butanol and 2-amino-2-methyl-1-propanol.

8. The composition of claim 2 wherein said one or more antimicrobial agents is N,N-dimethylaminoproyl tridecanoic ether.

9. The composition of claim 2 wherein said one or more antimicrobial agents is N,N-dimethylaminopropyl decanoic ether.

* * * * *